(12) United States Patent
Aalders et al.

(10) Patent No.: US 9,063,108 B2
(45) Date of Patent: Jun. 23, 2015

(54) NEEDLE INTERFACE FOR FLUID CONNECTIONS

(75) Inventors: Arnold Aalders, Waalwijk (NL); Adrianus Wilhelmus Dionisius Maria Van Den Bijgaart, Helvoirt (NL); Jozef Christiaan Mathieu Versleegers, Bree (BE); Ronald Cornelis De Gier, Eindhoven (NL); Petrus Henricus Maria Timmermans, Teteringen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1111 days.

(21) Appl. No.: 13/037,501

(22) Filed: Mar. 1, 2011

(65) Prior Publication Data

US 2011/0146421 A1 Jun. 23, 2011

Related U.S. Application Data

(62) Division of application No. 12/516,372, filed as application No. PCT/IB2007/054762 on Nov. 23, 2007, now abandoned.

(30) Foreign Application Priority Data

Dec. 1, 2006 (EP) ..................... 06125200

(51) Int. Cl.
*G01N 1/10* (2006.01)
*G01N 30/18* (2006.01)
(52) U.S. Cl.
CPC .......... *G01N 30/18* (2013.01); *G01N 2030/185* (2013.01)
(58) Field of Classification Search
None
See application file for complete search history.

(56) References Cited

U.S. PATENT DOCUMENTS

| 3,353,411 | A |   | 11/1967 | Nadeau |            |
|-----------|---|---|---------|--------|------------|
| 3,880,162 | A | * | 4/1975  | Simmons | ...... 604/197 |
| 3,884,230 | A | * | 5/1975  | Wulff  | ............ 604/198 |
| 3,976,070 | A | * | 8/1976  | Dumont | ........ 604/198 |
| 4,615,226 | A | * | 10/1986 | DiNuzzo et al. | ...... 73/864.87 |

(Continued)

FOREIGN PATENT DOCUMENTS

| EP | 0509281 A2 | 10/1992 |
| EP | 0761562 A1 | 3/1997 |

(Continued)

OTHER PUBLICATIONS

Definition of the term "bush" (listed as "4bush"), Merriam-Webster's Collegiate Dictionary, Tenth Edition, 1999.*

*Primary Examiner* — Robert R Raevis

(57) ABSTRACT

The invention relates to a coupling system that can particularly be applied for interfacing a consumable component with a sample chamber to a laboratory instrument for processing a sample fluid. The coupling system comprises a female interface module (10) integrated into the consumable component that has an elastic sealing component (12) with a preformed channel (12*a*). Moreover, it comprises a male interface module (20) integrated into the instrument and comprising a hollow needle (23) fixed in a first section (22*a*) of a bush (22), wherein the flexible free end of said needle (23) is partially surrounded by a second section (22*b*) of the bush that limits the lateral movement of the needle. The diameter of the channel in the sealing component (12) is preferably smaller than the diameter (d) of the needle (23), thus providing an airtight connection and a self-cleaning effect.

14 Claims, 1 Drawing Sheet

(56) References Cited

U.S. PATENT DOCUMENTS

| | | | |
|---|---|---|---|
| 4,624,148 A * | 11/1986 | Averette | 73/864.21 |
| 4,998,927 A | 3/1991 | Vaillancourt | |
| 5,265,483 A * | 11/1993 | Farrell et al. | 73/863.86 |
| 5,339,701 A | 8/1994 | Green | |
| 5,400,666 A * | 3/1995 | Song | 73/864.21 |
| 5,607,392 A | 3/1997 | Kanner | |
| 6,110,160 A * | 8/2000 | Farber | 604/412 |
| 6,145,967 A | 11/2000 | Langford | |
| 6,526,812 B2 | 3/2003 | Martin | |
| 6,595,960 B2 * | 7/2003 | West et al. | 604/181 |
| 7,314,759 B2 | 1/2008 | Bigalke | |
| 2002/0131902 A1 | 9/2002 | Levy | |
| 2002/0141904 A1 * | 10/2002 | Rosen et al. | 422/102 |
| 2004/0067169 A1 | 4/2004 | Krause | |
| 2005/0228362 A1 | 10/2005 | Vaillancourt | |
| 2006/0088446 A1 | 4/2006 | Heck | |

FOREIGN PATENT DOCUMENTS

| | | |
|---|---|---|
| EP | 1275957 A2 | 1/2003 |
| EP | 1652787 A1 | 5/2006 |
| JP | 2002365178 A | 12/2002 |
| WO | 9311696 A2 | 6/1993 |
| WO | 2005013883 A1 | 2/2005 |

* cited by examiner

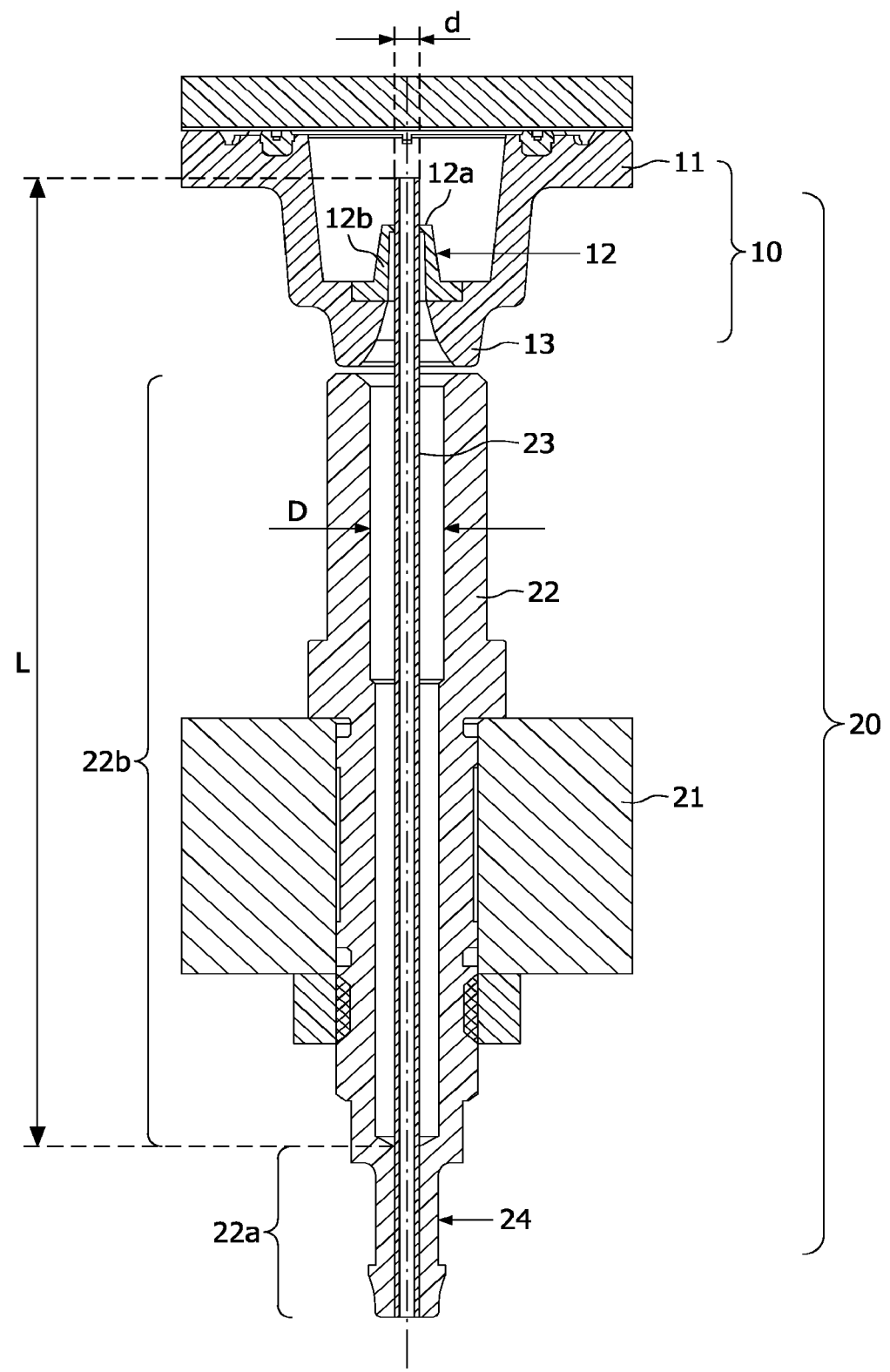

NEEDLE INTERFACE FOR FLUID CONNECTIONS

The invention relates to a female interface module and a compatible male interface module for establishing a fluid connection between two components, particularly between an instrument and consumables. Moreover, it relates to a consumable component and to an instrument comprising such interface modules.

Interface modules that can establish a fluid connection between two different components are particularly used in laboratory environments when fluid samples have to be processed. The U.S. Pat. No. 5,339,701 discloses in this respect a needle interface between a sampler unit and a gas chromatograph, wherein one of these instruments comprises a hole covered by a septum while the other instrument comprises a tapered hollow needle. The needle punctures the septum when a fluid connection between the instruments is established.

Based on this background it was an object of the present invention to provide an alternative needle interface that is particularly suited for laboratory environments, wherein it is desirable that a multitude of sample carriers can be coupled to an instrument with minimal handling effort.

This object is achieved by a female interface module according to claim 1, by a male interface module according to claim 5, by a coupling system according to claim 9, by a consumable component according to claim 10, and by an instrument according to claim 11. Preferred embodiments are disclosed in the dependent claims.

The female interface module according to the present invention serves for the reception of a needle and comprises an elastic sealing component with a preformed channel through which a needle can be pushed from an exterior side to an interior side of the sealing component. The preformed channel may in principle have any cross section, though a circular cross section is usually preferred. The cross section of the preformed channel may exactly correspond to the cross section of the needle to be received; preferably, the cross section of the channel is however smaller than that of the associated needle (the diameter of a circular cross section may for example be smaller than the diameter of a cylindrical needle). The channel is widened in this case if the needle is pushed through, thus providing a tight sealing of the needle within the channel. The diameter of the cross section of the preformed channel may even be zero when it contains no needle, i.e. the channel may simply be a cut or puncture through the material of the sealing component without removing such material.

The described female interface has the advantage that the force with which a needle must be pushed through a sealing component is reduced as the needle can follow a preformed channel and must not cut its own path through the material. This eases the handling for a user and relieves the stability requirements for the needle. Moreover, the needle can have a blunt tip, which reduces the risk of injury for the users.

In a preferred embodiment of the female interface module, the sealing component has a higher compliance in radial direction of its channel than in axial direction of the channel. The sealing component can therefore comparatively easy follow lateral movements of a needle in the preformed channel, while it is stiff in axial direction. If a needle is pushed through the channel, the sealing component will therefore not give away to the pressure in axial direction but keep its position, thus assisting the advancement of the needle.

According to a further development of the invention, the sealing component of the female interface module comprises a sleeve, wherein the preformed channel is disposed at (i.e. next to) one end of the sleeve. The internal diameter of said sleeve is preferably larger than the external diameter of the needle to allow a free passage of the needle. The sleeve may optionally project to the interior side of the sealing component. If there is a gas or liquid under an overpressure at the interior side of the sealing component, this will surround the sleeve and press it is against a needle in the channel. The sleeve has therefore a self-sealing effect.

The female interface module may further optionally comprise a funnel-shaped guiding element on the exterior side of the sealing component. The guiding element provides an entrance of a large diameter for capturing the tip of a needle and guiding it to the comparatively small entrance of the preformed channel. The guiding element therefore eases the connection procedure and helps to avoid a cumbersome threading of the needle.

The invention further relates to a male interface module comprising a hollow needle and a bush, wherein a first section of the needle is firmly embedded in a first section of the bush, and the needle comprises a free end that is in axial direction partially surrounded by a second section of the bush and that is flexible in radial direction (said axial and radial directions being by definition determined with respect to the axis of the needle); moreover, there is an intermediate space between the needle and the second section of the bush.

One advantage of this interface module is that the needle is firmly mounted in a bush and that its free end is (partially) protected by said bush. Furthermore, the radial or lateral compliance of the needle is advantageous if the needle has to be pushed through a hole, for example through the preformed channel in a female interface module of the kind described above. The needle can in this case be bent if it is not exactly aligned with the hole and finds its way in a kind of self alignment. Moreover, the lateral compliance of the needle reduces the risk of injuries.

In a preferred design of the aforementioned male interface module, the radial movement of the needle is limited by the second section of the bush to the range of elastic deformation of the needle. This means that the second section of the bush, which partially surrounds the free end of the needle, serves as a stop for the radial movement of the needle. It therefore prevents the needle from an excessive bending that would result in plastic deformation. The required effect can be achieved by appropriate dimensions of the needle and bush. Thus it is for example preferred that the length L of the free end of the needle is at least twenty times larger than the (external) diameter d of the needle, i.e. $L \geq 20 \cdot d$. Thus a relatively long part of the needle projects freely from the first section of the bush, thus providing a high compliance in lateral direction. It should be noted, however, that the compliance in lateral direction can alternatively or additionally also be achieved by using a flexible bush and/or by bearing the bush in a flexible way.

The tip of the free end of the needle is preferably blunt, i.e. without any sharp edges or apices. Such a blunt tip reduces the risk of injuries of a user and makes a particular protection of the needle in its unused state, e.g. by a cap, obsolete.

According to a further development of the invention, the male interface module comprises a tube connector that is in fluid communication with the interior of the needle and to which (by definition) a tube can be connected. The tube connector can for example be directly fixed or integrated to the bush that bears the needle.

The invention further relates to a coupling system that comprises modules of the kind described above, i.e. a female interface module with an elastic sealing component comprising a preformed channel and a male interface module comprising a hollow needle located in a bush having a laterally flexible free end. Moreover, the (internal) diameter of the preformed channel in the female interface module shall be smaller than the external diameter of the needle in the male interface module, thus guaranteeing a tight sealing of the needle when it is introduced into the preformed channel and further providing a self-cleaning effect of the exterior of the needle. It should be noted that, if the channel and/or the needle do not have circular cross sections, their "diameter" has to be defined appropriately, for example as the maximal distance between two points on the circumference of the cross section and/or the diameter of a circle having the same area as the cross section.

The invention further relates to a consumable component comprising a sample chamber in which a sample fluid can be provided and a female interface module of the kind described above. The consumable component can for example be used in laboratory procedures for the investigation of biological fluids (blood, saliva etc.). Due to the particular design of its interface module, such a consumable component can readily be accessed with the help of a needle.

The invention further relates to an instrument for processing a sample in an external sample chamber, said instrument comprising a male interface module of the kind described above. The instrument may favorably be used in combination with the aforementioned consumable component, as the preformed channel in the female interface module and the lateral flexibility of the hollow needle of the male interface module allow an easy coupling between these two components.

These and other aspects of the invention will be apparent from and elucidated with reference to the embodiment(s) described hereinafter. These embodiments will be described by way of example with the help of the accompanying drawing.

The only FIGURE shows a section through a coupling system according to the present invention comprising a consumable component with a female interface module and an instrument with a male interface module.

Though a coupling system according to the present invention will in the following be described with respect to a particular application in a laboratory environment, it can in principle be used in many other applications, too, for example in industrial production machines. The coupling system shown in the FIGURE comprises a female interface module 10 and a male interface module 20. The female interface module 10 is integrated into a consumable component 11, which is only partially depicted in the FIGURE as its particular design is irrelevant for the present invention. Similarly, the male interface module 20 is integrated into an instrument from which only a frame 21 is indicated in the FIGURE.

The consumable component is typically a disposable product that is used to perform one test, while the instrument is provided with all necessary equipment to perform the test. During the test fluids provided in the consumable typically have to be mixed, heated, cooled and transported. The transport of these fluids from one part of the consumable to the other may be realized e.g. by pressurized air. In order to apply pressure generated by the instrument to the consumable, the consumable and the instrument have to be equipped with air-interfaces. Furthermore, the transport of the fluids can be validated by measuring a pressure build-up with the instrument. For a good validation the aforementioned air-interfaces therefore need to be airtight. In known airtight interfaces between an instrument and a consumable component, a needle is used to pierce a closed membrane or septum. One disadvantage of this method is that the needle has to be sharp and therefore needs to be shielded from creating a risk of injury. Another disadvantage is that a membrane or septum is relatively stiff for lateral movements while it has to withstand the force needed to puncture it.

The coupling system shown in the FIGURE provides an improved airtight interface that avoids the aforementioned problems. The male interface module 20 of this system comprises a hollow needle 23 that is placed in a bush 22 in such a way that a first short section of the needle 23 (here the lower end of the needle) is fixed in a first section 22a of the bush, while the long residual "free end" of the needle 23 is free to move laterally. The free end is partially (preferably to more than 50% of its axial extension L) surrounded by a second section 22b of the bush 22. The internal diameter D of this second section 22b is larger than the external diameter d of the needle such that an annular clearance is formed around the needle. The end section of the needle 23 projects freely from the bush 22.

The fixation point of the needle 23 in the bush 22 is as far away from the free tip of the needle 23 as possible. The length L of the "free end" of the needle 23 is in the shown example more than 30-times larger than the external diameter d of the needle 23. This ensures that the needle 23 is flexible in lateral direction. Moreover, the internal diameter D of the second section 22b of the bush 22 is chosen such that it stops the lateral movement of the needle just before it would lead to an irreversible plastic deformation of the needle. At the upper end of the section 22b, the needle cannot move more than a distance $(D/2-d/2)$ to either side.

The outside of the needle 23 has preferably a smooth surface, while the tip of the needle 23 is blunt with its edges being de-burred to ensure a smooth entry of the needle 23 into the female interface module and to minimize the risk of injuries.

The needle 23 is for example glued or pressed into the first section 22a of the bush 22 to make the connection between bush 22 and needle 23 airtight and to fixate the needle 23 into the bush 22. Furthermore, the bush 22 is provided with a tube interface 24 that makes it possible to connect a tube (not shown) for an exchange of fluids with the interior of the needle 23. A typical material of the bush is stainless steel or a plastic.

The second part of the coupling system is the female interface module 10 in the consumable. This module 10 comprises a sealing component 12 that can for example be made from rubber or a similar elastic material and that comprises an open, preformed channel 12a which fits around the needle 23 to make an airtight interface. The diameter of the channel 12a in the sealing component 12 is (at rest) smaller than the external diameter d of the needle 23; it may for example have a value between 0% and 99% of the diameter d, most preferably between 50% and 99%. The sealing component 12 will thus have to stretch if the needle 23 is inserted and create an airtight interface. A lateral flexibility of the sealing component 12 makes sure that it can follow a side movement of the needle 23 without loosing its airtight capabilities. In axial direction of its channel, the sealing component 12 is however provided with some stiffness to prevent a needle 23 from pushing against instead of pushing through the sealing component 12.

The sealing component 12 optionally comprises a sleeve 12b that projects upward into the interior of the consumable and that carries the preformed channel 12a at its upper end. This sleeve 12b ensures an extra air-tightness when overpressure is applied in the interior of the consumable.

The female interface module 10 further comprises a guiding element 13 located on the exterior side of the sealing component 12, i.e. facing the instrument. The guiding element 13 is shaped in such a way (e.g. like a funnel) that the needle 23 can pre-align to the sealing component 12 and that it can act as a stop that limits the lateral movement of the needle 23 with respect to the sealing component 12.

The needle 23 and the bush 22 are commonly carried by a frame 21 of the instrument.

When a new interface is made between the instrument and the consumable, the needle 23 is pushed through the sealing component 12. As soon as the sealing component 12 has its airtight fit around the needle 23, it acts as a cleaner for the interface by pushing dirt particles ahead.

The described coupling system can be modified in various ways, for example:

- The needle 23 can additionally or alternatively be made flexible in lateral directions by making the bush 22 flexible.
- Instead of using a bush 22 to make the air connection, the air connection can also be made with the frame. The needle 23 can then be directly inserted into the frame, thus using less parts.
- The shape of the sealing component 12 can be different than shown, depending on the demands. Thus an o-ring might for example act as sealing component.

The coupling system can favorably be used in all instruments/products that need to make an airtight connection, for example in laboratory instruments or production equipment. It provides the following advantages:

- Due to the flexible needle 23 and the flexible sealing component 12, the coupling system can cope with movements between the instrument and the consumable, e.g. movements caused by thermal expansion.
- Due to the laterally flexible needle 23, the coupled components exert relative low forces onto each other.
- After insertion of the needle 23 through the sealing component 12, no forces are exerted between the coupled parts in axial direction of the needle 23.
- The interface is self-cleaning since dirt particles that may stick to the needle 23 are automatically pushed off the needle 23 each time a new interface is made.
- The shape of the sealing component 12 ensures extra airtightness when overpressure is applied.
- Since the needle 23 is inserted through the sealing component 12, the length of the needle 23 does not need to be accurate.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An interface module, comprising:
   a hollow needle; and
   a bushing,
   wherein a first section of the needle is firmly embedded in a first section of the bushing,
   wherein the needle comprises a free end that is partially surrounded with an intermediate space by a second section of the bushing that is flexible in a radial direction, and
   wherein radial movement of the needle is limited by the second section of the bushing to the range of elastic deformation of the needle.

2. The interface module of claim 1, wherein a tip of the free end of the needle is blunt.

3. The interface module of claim 1, wherein the bushing comprises a tube connector that is in fluid communication with an interior of the needle.

4. The interface module of claim 1, wherein the free end of the needle is, to more than 50% of its axial extension, surrounded by the second section of the bushing.

5. The interface module of claim 4, wherein a length of the free end of the needle is more than 30-times larger than an external diameter of the needle.

6. The interface module of claim 1, wherein a portion of the free end of the needle projects freely beyond an outer surface of the second section of the bushing.

7. A coupling system, comprising:
   a male interface module, comprising:
      a hollow needle; and
      a bushing,
      wherein a first section of the needle is firmly embedded in a first section of the bushing,
      wherein the needle comprises a free end that is partially surrounded with an intermediate space by a second section of the bushing that is flexible in a radial direction, and
      wherein radial movement of the needle is limited by the second section of the bushing to a range of elastic deformation of the needle; and
   a female interface module for reception of the needle, the female interface module comprising an elastic sealing component defining a channel configured for receiving the needle from an exterior side to an interior side of the elastic sealing component, wherein a diameter of the channel in the elastic sealing component when the needle is not disposed within the channel is smaller than an external diameter of the needle.

8. The coupling system of claim 7, wherein a tip of the free end of the needle is blunt.

9. The coupling system of claim 7, wherein the bushing comprises a tube connector that is in fluid communication with an interior of the needle.

10. The coupling system of claim 7, wherein the free end of the needle is, to more than 50% of its axial extension, surrounded by the second section of the bushing.

11. The coupling system of claim 7, wherein a length of the free end of the needle is more than 30-times larger than an external diameter of the needle.

12. The coupling system of claim 7, wherein a portion of the free end of the needle projects freely beyond an outer surface of the second section of the bushing.

13. The coupling system of claim 7, wherein the elastic sealing component has a higher compliance in a radial direction of the channel than in an axial direction of the channel.

14. The coupling system of claim 7, wherein the female interface module further comprises a funnel-shaped guiding element on an exterior side of the elastic sealing component.

* * * * *